United States Patent [19]

Lim et al.

[11] 4,243,803
[45] Jan. 6, 1981

[54] PRODUCTION OF 7-(2-AMINOMETHYL-PHENYLACETAMIDO)-3-(1-CARBOXYME-THYLTETRAZOL-5-YLTHIOMETHYL)-3-CEPHEM-4-CARBOXYLIC ACID

[75] Inventors: Gary M. F. Lim; Masaki Endo, both of Candiac, Canada

[73] Assignee: Bristol-Myers Company, New York, N.Y.

[21] Appl. No.: 54,733

[22] Filed: Jul. 5, 1979

[51] Int. Cl.³ .............................................. C07D 501/04
[52] U.S. Cl. ........................................ 544/26; 424/246
[58] Field of Search .................................. 544/26, 27

[56] References Cited

U.S. PATENT DOCUMENTS

| | | | |
|---|---|---|---|
| 2,860,167 | 11/1958 | Brown | 260/583 |
| 3,035,904 | 5/1962 | Brown | 44/57 |
| 4,100,346 | 7/1978 | Gottstein et al. | 260/243 C |
| 4,118,563 | 10/1978 | Lim et al. | 544/26 |

OTHER PUBLICATIONS

Burg et al., JACL 59, 780–787, (1937).
Suzuki, J. Amer. Chem. Soc. 93 4329–4330, (1971).
Lane, Aldrichimica Acta 6(3) 51–58, (1973).

*Primary Examiner*—Nicholas S. Rizzo
*Attorney, Agent, or Firm*—Herbert W. Taylor, Jr.

[57] ABSTRACT

Ceforanide is produced by the reduction in aqueous solution of a water-soluble salt 7-(2-azido-methylphenylacetamido)-3-(1-carboxymethyltetrazol-5-ylthiomethyl)-3-cephem-4-carboxylic acid using a borane-amine complex and Raney nickel.

40 Claims, No Drawings

PRODUCTION OF 7-(2-AMINOMETHYLPHENYLACETAMIDO)-3-(1-CARBOXYMETHYLTETRAZOL-5-YLTHIOMETHYL)-3-CEPHEM-4-CARBOXYLIC ACID

BACKGROUND OF THE INVENTION

1. Field of the Invention

This invention relates to the production by a novel chemical synthesis of particular members of the cephalosporin family of antibiotics characterized by having 2-aminomethylphenylacetamido as their 7-substituent.

2. Description of the Prior Art 7-(2-Aminomethylphenylacetamido)-3-(1-carboxymethyltetrazol-5-ylthiomethyl)-3-cephem-4-carboxylic acid is a potent injectable cephalosporin having the generic name ceforanide; it has also been called BL-S786 in the literature. It was described, for example, in U.S. Pat. No. 4,100,346.

U.S. Pat. No. 4,118,563 describes the preparation of ceforanide by the reduction with hydrogen and Raney nickel of the corresponding 2-azidomethyl compound.

Older preparations and uses of hydrides of boron were described, for example, by Burg and Schlesinger, J. Amer. Chem. Soc. 59, 780–787 (1937). Complexes of $BH_3$ (also called borine) with amines were disclosed by Brown in U.S. Pat. Nos. 2,860,167 and 3,035,904. The borane-amine complexes were reviewed by Lane in Aldrichimica Acta, 6(3), 51–58 (1973) and many of them are commercially available. For the use of boranes (but not the amine complexes) to reduce organic azides to secondary amines see Suzuki, J. Amer. Chem. Soc. 93, 4329–30 (1971).

The object of the present invention was to provide a process similar to that of U.S. Pat. No. 4,118,563 which did not require the use on a commercial scale of expensive special equipment used for that type of hydrogenation.

SUMMARY OF THE INVENTION

There is provided by the present invention the process for the production of the cephalosporin having the formula

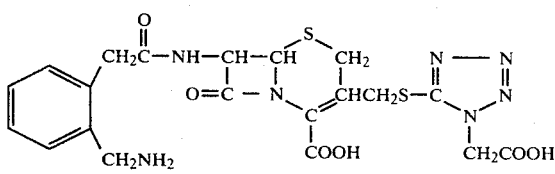

which comprises the consecutive steps of (a) mixing an aqueous solution having a pH of about 7 of a water-soluble salt, preferably the N-methylmorpholine salt, of the starting compound of the formula

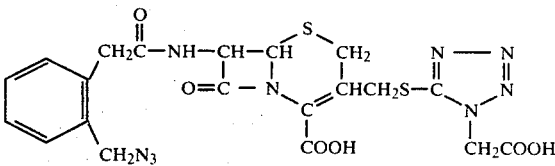

with water-washed, neutral Raney nickel (preferably by adding said aqueous solution in small portions to the Raney nickel under nitrogen) and then (b) adding, preferably at about room temperature and under nitrogen, to the mixture thus formed a small molar excess, e.g. 1.1 to 2.0 moles and preferably about 1.5 moles, per mole of said starting material of a boraneamine complex, preferably borane-N,N-diethylaniline complex, borane-trimethylamine complex, borane-triethylamine complex, borane-pyridine complex, borane-morpholine complex, borane-N-phenylmorpholine complex, borane-tert.-butylamine complex, borane-dimethylamine complex or borane-2,6-lutidine complex, and (c) stirring the mixture at about room temperature until said starting compound has been substantially completely converted to the desired final product.

The reaction is conducted at atmospheric pressure and does not require the use of gaseous hydrogen or a pressure vessel. Complete reduction is achieved rapidly, e.g. in one or two hours.

DESCRIPTION OF THE PREFERRED EMBODIMENTS

EXAMPLE 1

7-(2-Azidomethylphenylacetamido)-3-(1-carboxymethyltetrazole-5-ylthiomethyl)-3-cephem-4-carboxylic acid (6.45 g., 0.01 mole) prepared according to U.S. Pat. No. 4,118,563 was dissolved in 50 ml. water by the addition of N-methylmorpholine to pH 7. This solution was added to Raney nickel (6 g. wet weight, previously washed until neutral with water) under nitrogen at such a rate as to keep foaming from becoming excessive. After the addition was completed and the foaming stabilized one gram of boron-trimethylamine complex was added and the mixture was stirred at room temperature for 90 minutes. The Raney nickel was filtered off and the filtrate was acidified to pH 2.5 with 6N HCl and stirred under nitrogen for one hour at room temperature. The product, 7-(2-aminomethylphenylacetamido)-3-(1-carboxymethyltetrazol-5-ylthiomethyl)-3-cephem-4-carboxylic acid was collected by filtration, dried in vacuo, and found to weigh 3 g. and to have an infrared absorption spectrum consistent with that structure.

EXAMPLE 2

7-(2-Azidomethylphenylacetamido)-3-(1-carboxymethyltetrazol-5-ylthiomethyl)-3-cephem-4-carboxylic acid (6.45 g., 0.01 mole) was dissolved in 50 ml. water by the addition of N-methylmorpholine to pH 7. This solution was added to Raney nickel (6 g. wet weight, previously washed until neutral with water) under nitrogen at such a rate as to keep foaming from becoming excessive. After the addition was completed and the foaming stabilized 1.4 g. (0.015 mole) pyridine-borane complex (Aldrich) was added. The resulting solution was stirred at room temperature for 90 minutes and then filtered through diatomaceous earth. The filtrate (pH 7.9) was acidified with 6N HCl to pH 2.5 and the resulting slurry was stirred at room temperature for 30 minutes and then in an ice-bath for another 30 minutes. The product, 7-(2-aminomethylphenylacetamido)-3-(1-carboxymethyltetrazol-5-ylthiomethyl)-3-cephem-4-carboxylic acid, was collected by filtration, washed with about 10 ml. water and dried in a vacuum desiccator overnight to yield 2.93 g. (56.5% yield). Infrared absorption spectra indicated completion of reduction.

EXAMPLE 3

7-(2-Azidomethylphenylacetamido)-3-(1-carboxymethyltetrazol-5-ylthiomethyl)-3-cephem-4-carboxylic acid (6.45 g., 0.01 mole) was dissolved in 50 ml. water by the addition of N-methylmorpholine to pH 7. This solution was added dropwise over 15 minutes to Raney nickel (6 g. wet weight, previously washed until neutral with water) under nitrogen at such a rate as to keep foaming from becoming excessive. After the addition was completed and the foaming stabilized 2.45 g. (0.015 mole) N,N-diethylaniline-borane complex (Aldrich) was added. The resulting solution was stirred at room temperature for 90 minutes and then filtered through diatomaceous earth. The filtrate (pH 7.2) was acidified with 6N HCl to pH 2.5 and the resulting slurry was stirred at room temperature for 30 minutes and then in an ice-bath for another 30 minutes. The product, 7-(2-aminomethylphenylacetamido)-3-(1-carboxymethyltetrazol-5-ylthiomethyl)-3-cephem-4-carboxylic acid was collected by filtration, washed with about 10 ml. water and dried in a vacuum desiccator overnight to yield 3.27 g. (63% yield). Infrared absorption spectra indicated completion of reduction.

The borane-diethylamine complex, the borane-N,N-diethylaniline complex, the borane-triethylamine complex and the borane-pyridine complex are preferred because they are stable, neat liquids. It is desirable that the pH during the reduction be between 6 and 7.5.

COMPARISON EXAMPLES (a) Sodium borohydride as hydrogen source.

Using the procedure of the examples above the reduction was carried out using sodium borohydride in water and Raney nickel as catalyst. The reduction proceeded smoothly but the product was isolated in low yield. In this case it was not possible to control the pH of the reaction mixture even when the N-methylmorpholine salt was used.

(b) Sodium cyanoborohydride as hydrogen source.

Using the procedure of the examples above the reduction was carried out using sodium cyanoborohydride in water and Raney nickel as catalyst. The pH of the reaction mixture in this case stopped at 7.8 but the reduction proceeded at a slower rate. The isolated yield was also low.

This invention is capable of industrial utilization.

We claim:

1. The process for the production of the cephalosporin having the formula

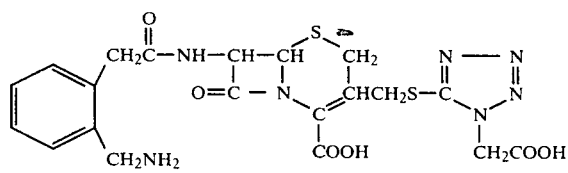

which comprises the consecutive steps of (a) mixing an aqueous solution having a pH of about 7 of the starting compound of the formula

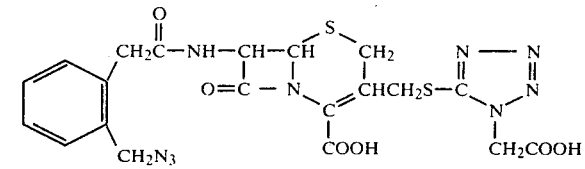

with water-washed, neutral Raney nickel and then (b) adding to the mixture thus formed a small molar excess compared to said starting material of a borane-amine complex and (c) stirring the mixture at about room temperature until said starting compound has been substantially completely converted to the desired final product.

2. The process of claim 1 wherein the borane-amine complex is the borane-N,N-diethylaniline complex.

3. The process of claim 1 wherein the borane-amine complex is the borane-trimethylamine complex.

4. The process of claim 1 wherein the borane-amine complex is the borane-triethylamine complex.

5. The process of claim 1 wherein the borane-amine complex is the borane-pyridine complex.

6. The process of claim 1 wherein the borane-amine complex is the borane-morpholine complex.

7. The process of claim 1 wherein the borane-amine complex is the borane-N-phenylmorpholine.

8. The process of claim 1 wherein the borane-amine complex is the borane-tert. butylamine complex.

9. The process of claim 1 wherein the borane-amine complex is the borane-dimethylamine complex.

10. The process of claim 1 wherein the borane-amine complex is the borane-2,6-lutidine complex.

11. The process for the production of the cephalosporin having the formula

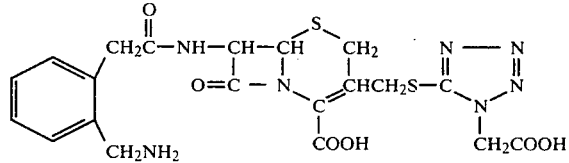

which comprises the consecutive steps of (a) mixing an aqueous solution having a pH of about 7 of a water-soluble salt of the starting compound of the formula

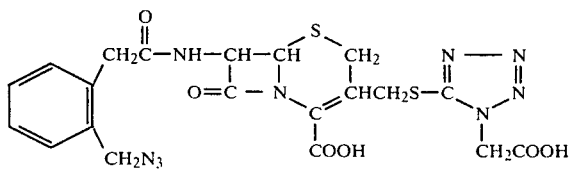

with water-washed, neutral Raney nickel by adding said aqueous solution in small portions ot the Raney nickel under nitrogen and then (b) adding to the mixture thus formed a small molar excess, compared to said starting material of a borane-amine complex, and (c) stirring the mixture at about room temperature until said starting compound has been substantially completely converted to the desired final product.

12. The process of claim 11 wherein the borane-amine complex is the borane-N,N-diethylaniline complex.

13. The process of claim 11 wherein the borane-amine complex is the borane-trimethylamine complex.

14. The process of claim 11 wherein the borane-amine complex is the borane-triethylamine complex.

15. The process of claim 11 wherein the borane-amine complex is the borane-pyridine complex.

16. The process of claim 11 wherein the borane-amine complex is the borane-morpholine complex.

17. The process of claim 11 wherein the borane-amine complex is the borane-N-phenylmorpholine complex.

18. The process of claim 11 wherein the borane-amine complex is the borane-tert butylamine complex.

19. The process of claim 11 wherein the borane-amine complex is the borane-dimethylamine complex.

20. The process of claim 11 wherein the borane-amine complex is the borane-2,6-lutidine complex.

21. The process for the production of the cephalosporin having the formula

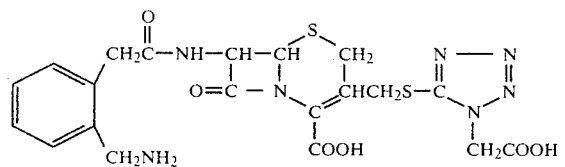

which comprises the consecutive steps of
(a) mixing an aqueous solution having a pH of about 7 of the N-methylmorpholine salt of the starting compound of the formula

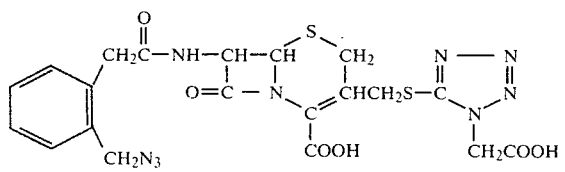

with water-washed, neutral Raney nickel by adding said aqueous solution in small portions to the Raney nickel under nitrogen and then
(b) adding to the mixture thus formed a small molar excess compared to said starting material of a borane-amine complex and
(c) stirring the mixture at about room temperature until said starting compound has been substantially completely converted to the desired final product.

22. The process of claim 21 wherein the borane-amine complex is the borane-N,N-diethylaniline complex.

23. The process of claim 21 wherein the borane-amine complex is the borane-trimethylamine complex.

24. The process of claim 21 wherein the borane-amine complex is the borane-triethylamine complex.

25. The process of claim 21 wherein the borane-amine complex is the borane-pyridine complex.

26. The process of claim 21 wherein the borane-amine complex is the borane-morpholine complex.

27. The process of claim 21 wherein the borane-amine complex is the borane-N-phenylmorpholine complex.

28. The process of claim 21 wherein the borane-amine complex is the borane-tert. butylamine complex.

29. The process of claim 21 wherein the borane-amine complex is the borane-dimethylamine complex.

30. The process of claim 21 wherein the borane-amine complex is the borane-2,6-lutidine complex.

31. The process for the production of the cephalosporin having the formula

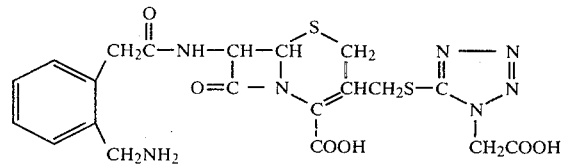

which comprises the consecutive steps of
(a) mixing an aqueous solution having a pH of about 7 of a water-soluble salt of the starting compound of the formula

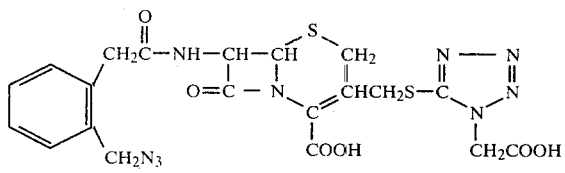

with water-washed, neutral Raney nickel by adding said aqueous solution in small portions to the Raney nickel under nitrogen and then
(b) adding to the mixture thus formed 1.1 to 2.0 moles per mole of said starting material of a borane-amine complex and
(c) stirring the mixture at about room temperature until said starting compound has been substantially completely converted to the desired final product.

32. The process of claim 31 wherein the borane-amine complex is the borane-N,N-diethylaniline complex.

33. The process of claim 31 wherein the borane-amine complex is the borane-trimethylamine complex.

34. The process of claim 31 wherein the borane-amine complex is the borane-triethylamine complex.

35. The process of claim 31 wherein the borane-amine complex is the borane-pyridine complex.

36. The process of claim 31 wherein the borane-amine complex is the borane-morpholine complex.

37. The process of claim 31 wherein the borane-amine complex is the borane-phenylmorpholine complex.

38. The process of claim 31 wherein the borane-amine complex is the borane-tert. butylamine complex.

39. The process of claim 31 wherein the borane-amine complex is the borane-dimethylamine complex.

40. The process of claim 31 wherein the borane-amine complex is the borane-2,6-lutidine complex.

* * * * *